United States Patent
Stoller et al.

[11] Patent Number: 5,841,135
[45] Date of Patent: *Nov. 24, 1998

[54] METHOD AND APPARATUS FOR MEASURING FORMATION DENSITY AND THE FORMATION PHOTO-ELECTRIC FACTOR WITH A MULTI-DETECTOR GAMMA-GAMMA TOOL

[75] Inventors: Christian Stoller, Kingwood; Nihal I. Wijeyesekera, Stafford; Urmi DasGupta, Houston; Donald C. McKeon, Katy, all of Tex.; Peter D. Wraight, Ridgefield, Conn.

[73] Assignee: Schlumberger Technology Corporation, Houston, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 800,976

[22] Filed: Feb. 19, 1997

[51] Int. Cl.⁶ ........................................ G01V 5/12
[52] U.S. Cl. ........................................ 250/269.3; 250/266
[58] Field of Search .................... 250/265, 266, 250/264, 269.3

[56] References Cited

U.S. PATENT DOCUMENTS

| | | |
|---|---|---|
| 3,321,625 | 5/1967 | Wahl . |
| 4,048,495 | 9/1977 | Ellis . |
| 4,129,777 | 12/1978 | Wahl et al. . |
| 5,334,833 | 8/1994 | Case et al. . |
| 5,390,115 | 2/1995 | Case et al. . |
| 5,525,797 | 6/1996 | Moake . |
| 5,528,029 | 6/1996 | Chapellat et al. ................. 250/266 |
| 5,530,243 | 6/1996 | Mathis . |
| 5,596,191 | 1/1997 | Mickael . |
| 5,635,712 | 6/1997 | Scott, III et al. ................. 250/260 |
| 5,659,169 | 8/1997 | Mickael . |

FOREIGN PATENT DOCUMENTS 0206593  12/1986  European Pat. Off. .

*Primary Examiner*—David P. Porta
*Attorney, Agent, or Firm*—Brigitte L. Jeffery; John J. Ryberg

[57] ABSTRACT

The present invention is an improved method and tool for determining formation density by using an array of gamma-ray detectors. This invention can correct for large standoffs encountered in abnormally shaped boreholes and in particular for the increased standoffs typically encountered by mandrel tools. In this invention, the collimated detectors have varying depths of investigation into the formation. At small standoffs a short spaced (SS) detector investigates mainly the mud and mudcake and a shallow layer of the formation. Unlike the SS, a mid spaced (MS) detector has a deeper depth of investigation and is sensitive to borehole and formation even at increased standoffs. A long spaced (LS) detector is mainly sensitive to the formation density and its density reading is corrected by using the standoff information from the MS and SS detectors. In addition to measuring density, this invention can measure the photoelectric factor (PEF) of the formation. Because photoelectric absorption preferentially removes low energy gamma-rays, the tool housing needs to allow passage of low energy gamma-rays. This can be accomplished through the use of a window of a material with a low atomic number (Z) or through the use of a low-Z housing material like titanium. Typical window materials are beryllium and titanium. Housing materials can be titanium or for lower pressure requirements graphite or high-strength carbon compounds.

23 Claims, 4 Drawing Sheets

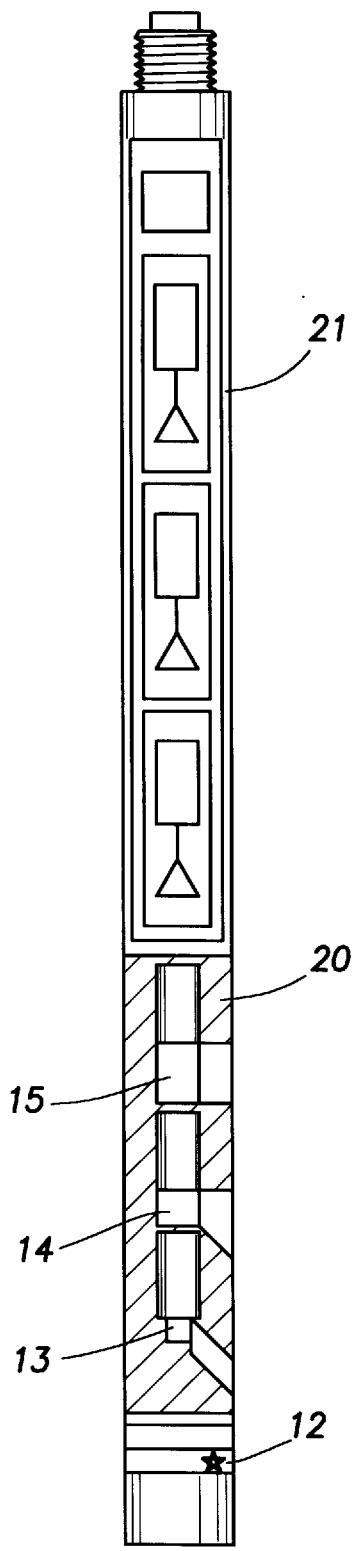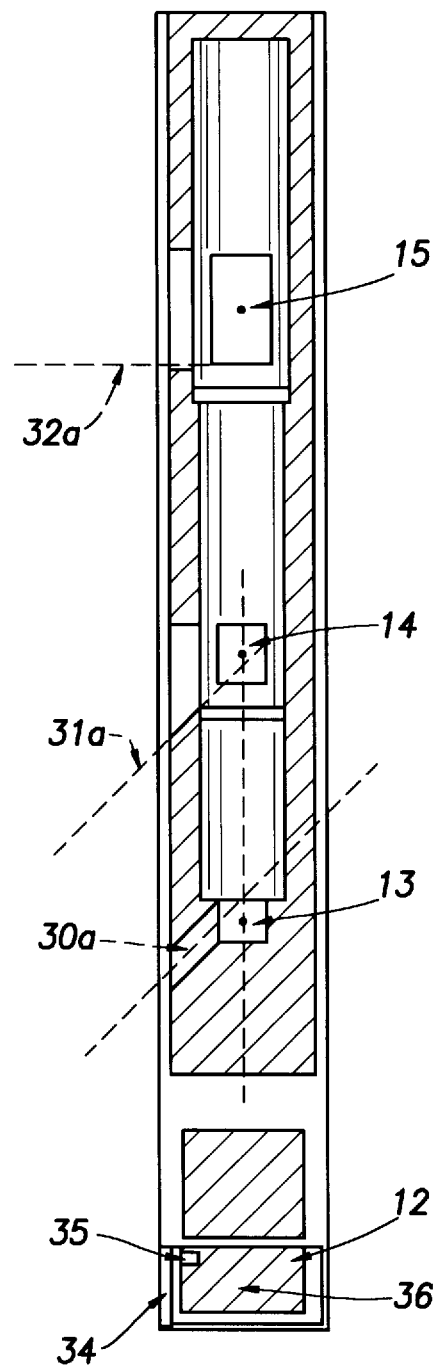

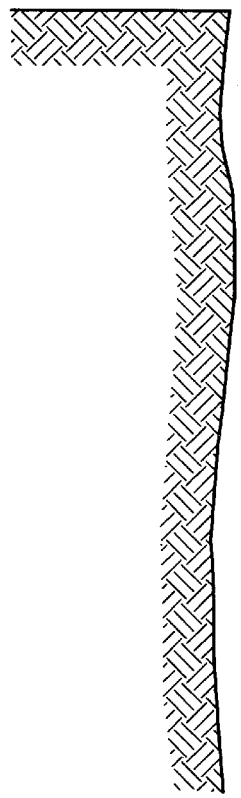
FIG.6
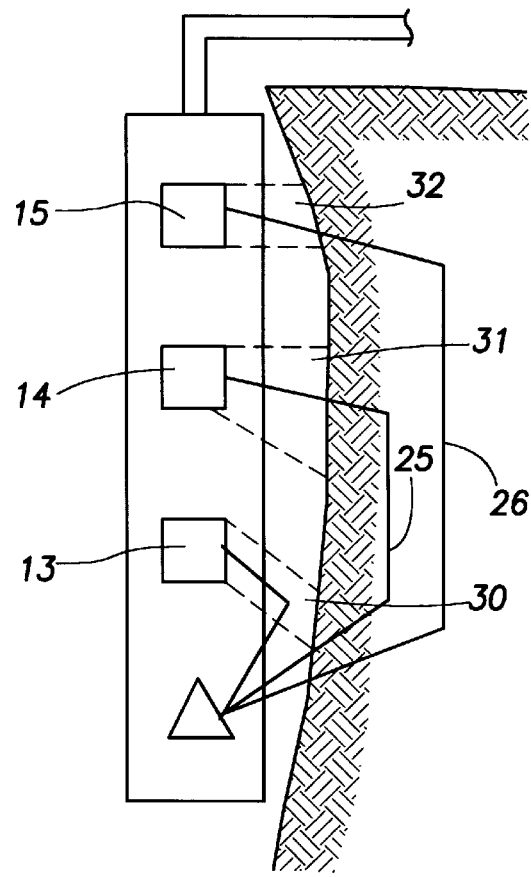
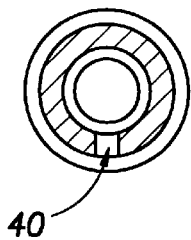
FIG.8a
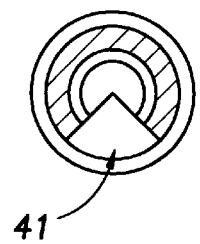
FIG.8b
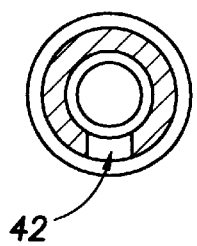
FIG.8c
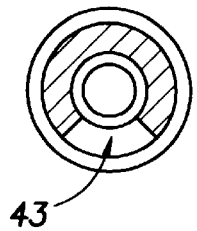
FIG.8d
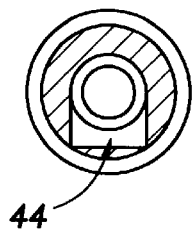
FIG.8e

METHOD AND APPARATUS FOR MEASURING FORMATION DENSITY AND THE FORMATION PHOTO-ELECTRIC FACTOR WITH A MULTI-DETECTOR GAMMA-GAMMA TOOL

FIELD OF THE INVENTION

This invention relates to the determination of an earth formation density and lithology of an earth formation. In particular, it relates to the determination of formation density using a three detector array which allows for the measurement of formation densities even at an extended standoff between the apparatus and the formation and which measures the photo-electric factor of a formation.

BACKGROUND OF THE INVENTION

Nuclear tools have been used for several decades to determine the density of earth rock formations surrounding a borehole. The nuclear density tools rely on the Compton scattering of gamma-rays in the formation for the density measurements. A conventional density tool consists of a source of gamma-rays (or X-rays), at least one gamma-ray detector and shielding between the detector and the source, so that only scattered gamma-rays are detected. During density logging, gamma-rays from the tool source travel through the borehole, into the earth formation. The gamma-rays will be scattered by the electrons in the formation or the borehole and some of them will be scattered back to the detector in the logging tool. Depending on the spacing between the source and detector, the count rate of detected gamma-rays will either increase with increasing formation density (scattering term dominant) or decrease with increasing formation density (attenuation effect predominant). At intermediate spacings, both attenuation and scattering terms influence the response.

In an ideal logging situation, the borehole would have a uniform and straight shape. This uniform borehole would enable a density tool containing a detector to be in close proximity with the formation surrounding the borehole and there would be minimal tool standoff. Under these conditions, one detector would be sufficient for the for a density measurement.

However, because boreholes normally do not have a uniform and straight shape, one major concern in density logging is the logging tool contact with the borehole wall. Density logging tools can be engineered either as pad tools or as mandrel tools. In a mandrel tool the source and detectors are in the body of the straight cylindrical tool. The long stiff length of such an arrangement renders it difficult for the tool to stay in close contact with a non-uniform borehole wall. In pad tools, the detectors and, in most cases, also the logging source are mounted in a short, articulated pad which can move with respect to the tool body. A strong eccentralizer arm pushes the pad against the borehole wall and allows much better contact because of the much smaller length of the device. All density logging tools will also encounter mudcake built up on the formation wall, which prevents good contact. The density measurement needs to be compensated for this kind of standoff as well. Because of the shortcomings of the mandrel tools, these tools are only used if a pad tool cannot be engineered because of size or cost constraints.

Most modern density tools use an articulated pad which houses the detectors and the gamma-ray source. A backup arm pushes the pad against the formation. The short length of such a pad and the large eccentralizing force exerted by the backup arm assure very good contact of the pad with the formation in most circumstances. However, for tools with a small diameter, the use of a pad type construction becomes difficult or impossible. In these cases, the detectors are placed inside the tool housing (mandrel tool). Eccentralization is provided by a bow-spring and/or a caliper device with a backup arm. However, the much longer stiff length of the tool leads to a poorer application of the tool to the borehole wall and leads to a larger average standoff.

The basic layout for a two detector tool is shown in FIG. 1. The tool 1 consists of a gamma-ray source 2, a short spaced (SS) detector 3 and a long spaced (LS) detector 4. The tool is in a borehole 5 that is substantially uniform. Gamma-rays emitted from the source 2 go into the borehole and formation 6, where they are scattered and some of them are subsequently detected by the detectors. The SS detector 3 is more sensitive to the region close to the tool 7. The LS detector 4 detects gamma-rays 8 from the formation 6 at greater depth than the SS detector and is less sensitive to effects of tool standoff. The apparent density derived from the LS detector measurement can be corrected for tool stand off by comparing the apparent density readings of the LS and SS detectors.

The correction for standoff caused by mudcake build-up or tool standoff can be accomplished by using two detectors with different depths of investigation. In this case, the first detector (SS) has a shallow depth of investigation and is more sensitive to the borehole fluid or mudcake between the tool and the formation. A second detector (LS) at a longer distance from the source is less sensitive to the borehole environment and is more sensitive to the formation. The difference between the two detector readings can be transformed into a correction for standoff and mudcake. However, at larger standoffs the 2-detector compensation is often insufficient or ambiguous.

The shortcomings of the 2-detector measurement lie in the fact that the two detector measurement is used to determine three unknowns: Formation density, standoff (distance between the tool and the borehole wall) and the density of the fluid and/or mudcake between the tool and the formation. At small standoffs the latter two unknowns can be combined into an effective thickness (mud density*standoff). At larger standoffs this approach fails and the correction becomes ambiguous. In addition, the short space detector depth of investigation can become smaller than the stand off. This will prevent proper compensation.

The situation of a large standoff is illustrated in FIG. 2. The two detector tool 1 is located in the borehole 5. Because of the irregular shape of the borehole wall 9 the tool is separated from the wall by a large distance. The short space detector 3 depth of investigation is smaller than the standoff and an effective compensation of the density answer of the long space detector 4 is more difficult and sometimes impossible.

The use of an additional detector positioned between the traditional LS and SS detectors can help in addressing the ambiguity of the correction at large tool stand off and some of the limitations of the two-detector tool can be overcome. The three-detector measurement provides the ability to distinguish the effect of the mud and/or mudcake thickness from the effect of the density of the mud/or and mudcake between the tool and the formation. In addition, the better statistical precision provided by the middle measurement will improve the logging speed of the tool. The operation of a three-detector tool is shown in FIG. 3. The three-detector tool 11 has the ability to measure three distinct depths of investigation in the formation. The tool has a source 12, and short spaced (SS) 13, middle spaced (MS) 14 and long spaced (LS) 15 detectors.

The idea of using three detectors to differentiate different depths of investigation was described in U.S. Pat. No. 4,129,777 (Wahl). In Wahl, the main idea is to measure the density of material at three different depths from the tool. This can be used for determining formation density through casing, for determining the cement thickness behind casing or for determining mudcake density and thickness between the tool and the formation. In all three cases the measurement is also used to determine the formation density and the thickness and density of the a layer of material between the tool and the formation.

In Wahl, gamma radiation is emitted from the tool into the surrounding media and measurements are taken of the amount of radiation which returns to the detectors as a result of the interaction of the emitted radiation with first, second and third layers respectively of the surrounding media each beginning at the borehole and extending to increasing radial depths. These measurements are taken by three detectors located at different spacings from the gamma radiation source so as to have three different depths of investigation. A representation of the thickness of the solid matter is then obtained from the three gamma radiation measurements.

In particular, the method proposed by Wahl is useful for determining the thickness of the bonding material between a borehole casing and the adjacent formation. In that case, the three gamma radiation measurements (shallow, intermediate and deep) are corrected for the attenuating effect of the casing. Three densities are then computed from the shallow, intermediate and deep radiation measurements respectively.

Another patent incorporating the three detector concept is U.S. Pat. No. 5,525,797, Moake. In this patent, like in Wahl, the gamma-ray source is spaced axially from the first, second and third detectors. The first/near detector is axially spaced from the gamma source by a distance defined as a first spacing. The first spacing and collimation for the first detector are designed so that the gamma-rays detected at the first detector are those gamma-rays that are scattered primarily by the casing.

A second or middle detector is spaced axially farther away from gamma-ray source than the first detector. The second detector is spaced from the gamma-ray source by a distance defined as a second spacing. The second spacing and collimation for the second detector are designed so that the gamma-rays detected at the second detector will be those that are primarily scattered by the casing and the cement. Finally, a third or far detector is spaced axially farther away from the gamma-ray source than both the first and second detectors by a distance defined as a third spacing. The third spacing and collimation defined by the third detector are designed so that the gamma-rays detected at the third detector are those primarily scattered from the casing, cement and formation. It is this third detector that enables the tool to measure formation density while the first and second detectors primarily enable the tool to correct for casing and cement. However, the second detector can be used to measure formation density in the absence of cement.

Preferably, the detectors are shielded by a high density material between the source and the detector that prevents detection of gamma-rays that are simply traveling up through the tool. A pathway or void in the shielding is provided in the form of a collimation channel which extends from the detector through the tool and terminates at the outside surface of the tool. The collimation channels are specifically designed for the detection scheme of each detector. Specifically, the near or first detector will have a collimation that is aimed at a small angle with respect to the casing so that the first detector will detect gamma-rays that are scattered mainly by the casing. The second or middle detector will have a collimation that is directed at a steeper or more perpendicular angle with respect to the casing because the second detector is intended to detect gamma-rays scattered through all of the cement as well as the casing (deeper depth of investigation). Finally, the third or far detector will have a wide collimation channel which is directed substantially perpendicular to the casing due to the distance of the third detector from the source. Because gamma-rays detected at the far detector must pass through the casing, cement, formation before passing back through the cement and casing, the statistical probability of this event happening is smaller than for the first and second detectors and therefore a wider collimation channel is required for the third detector.

The three detector density presented by Wahl describes the general idea of using three detectors to measure density in the presence of a material of substantial thickness and/or density between the tool and the formation. The distinction between different depth of investigation is achieved by the different axial spacing of the detectors.

The invention presented by Moake uses substantially the same detector spacings as the invention of Wahl. The detector collimation is optimized for a through casing measurement. The SS (first) and LS (third) detectors use collimation which is very similar to the one used in traditional two-detector density tools. The MS (middle) detector collimation is very tight and almost perpendicular to the borehole wall to get a deeper density reading in through-casing measurements. The steep collimation angle of the MS detector reduces its count rate and statistical precision. In an open hole measurement the depth of investigation of the MS and LS detectors will become very similar and the sensitivity to mudcake, which has a much smaller density than the steel casing, is reduced.

There remains a need for a solution to determining a correction for standoff in logging tools that can overcome these limitations. The present invention provides a multi-detector measurement optimized for situations in which a density tool encounters substantial standoff from the formation. Although optimized for open hole logging the tool can be used in cased hole logging as well. In order to achieve this goal the tool uses an optimized set of collimators for the short, middle and long spaced detectors. In particular, the collimation of the middle detector is different from the collimations of the short spaced or long spaced detectors. This provides the correct depth of investigation for the middle detector, i.e. a depth of investigation intermediate between the short spaced and the long spaced detectors. In addition this kind of collimation is well suited for a high precision density measurement and for an optimized measurement of the photoelectric effect.

In addition to measuring density, most modern nuclear density tools also measure the photo-electric factor (PEF) of the formation. This measurement relies on the absorption of low energy gamma-rays through the photoelectric effect in the formation. Since the photo-electric effect depends strongly on the atomic number of the formation elements, it provides an indication of the lithology of the formation. Because photo-electric absorption preferentially removes low energy gamma-rays, the tool housing needs to allow passage of low energy gamma-rays to detectors inside the housing. This objective can be accomplished through the use of a window of a material with a low atomic number (Z) in the housing or through the use of a low-Z housing material like titanium. Typical window materials are beryllium and titanium. Housing materials can be titanium or for lower pressure requirements graphite or high-strength carbon compounds.

SUMMARY OF THE INVENTION

It is an object of this invention to provide an optimized means to make an high-quality density measurement in the presence of large tool standoff.

It is another object of this invention to provide a slimmer (mandrel) logging tool with a measurement quality which is at least as good as the one of traditional two-detector pad tools.

It is another object of this invention to provide an improved means to detect the photo-electric effect of an earth formation.

It is another object of the tool to provide a two or three detector photo-electric measurement compensated for standoff.

The present invention is an improved method and tool for determining formation density by using an array of gamma-ray detectors. This tool has improved standoff correction, better precision and significantly enhanced measurement for photo-electric effect. In addition, this tool has a slimmer diameter than conventional logging tools. This invention can correct for large standoffs encountered in abnormally shaped boreholes and in particular for the increased standoffs typically encountered by mandrel tools. In operation, three or more collimated detectors detect gamma-rays emitted from the tool source. In accordance with the tool design, the detectors have varying depths of investigation into the formation. At small standoffs, the SS detector investigates mainly the mud and mudcake and a shallow layer of the formation. As the standoff increases the SS detector signal is no longer sensitive to the formation or to the mud or mudcake found in close proximity to the formation. The MS detector has a deeper depth of investigation and is sensitive to borehole and formation even at increased tool standoffs. The long spaced (LS) detector is mainly sensitive to the formation density. This LS density reading is corrected by using the information from the MS and SS detectors to provide a more accurate density reading.

The present invention is also an improved method to determine the photo-electric factor (PEF) of the formation. The use of an array of three detectors in a titanium housing provides a high quality PEF answer, which is more precise and more accurate than in traditional two-detector tools, although the reduced tool diameter does not allow the use of low-Z windows for the low energy gamma-rays.

BRIEF DESCRIPTION OF THE DRAWINGS

FIG. 4 is a schematic view of the density tool implemented in the present invention.

FIG. 6 is a diagram of the detector collimation in a logging tool which implements the present invention.

FIG. 7 is a diagram of the detector section of a logging tool implemented in the present invention FIG. 8a is a cross sectional view of the short spaced detector collimation.

FIG. 8b is a cross sectional view of a possible middle detector collimation.

FIG. 8c shows an alternate middle detector collimation.

FIG. 8d is a cross sectional view of a possible far detector collimation.

FIG. 8e shows an alternate far detector collimation

DETAILED DESCRIPTION OF THE INVENTION

The basic tool layout is shown in FIG. 4. The tool consists of two sections: a sonde section 20 with the detectors 13, 14 and 15 and the gamma-ray source 12 and electronics section 21 with the nuclear amplifiers, analog to digital converters and auxiliary circuits for the tool operation. Although the figure shows a mandrel tool, the sonde design could be implemented in a pad tool.

Figure 1:
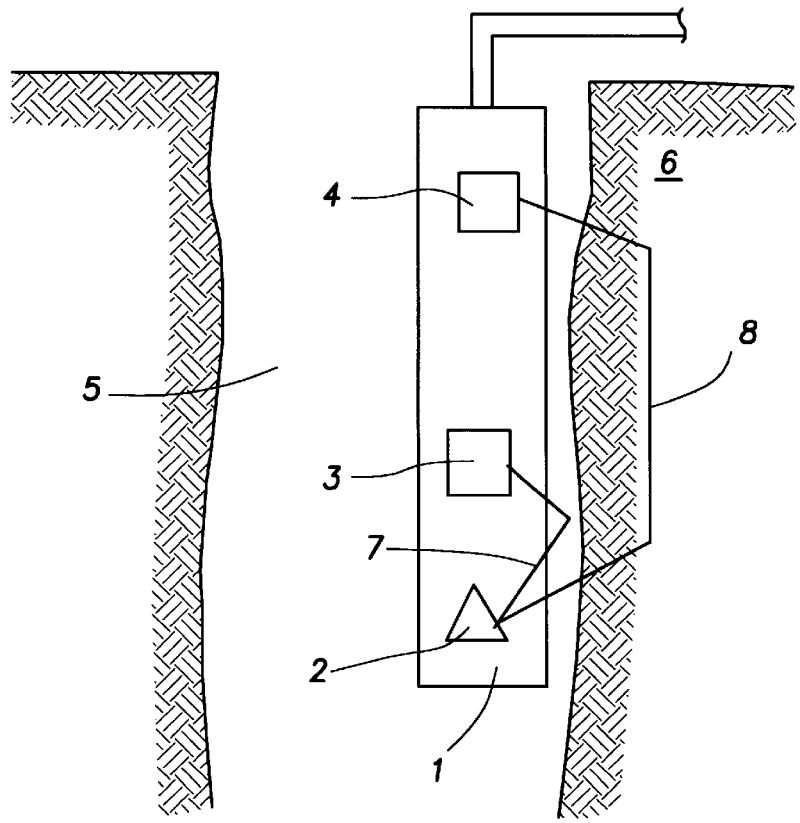
FIG. 1 is a diagram of a logging tool that detects gamma-rays using two detectors.
Figure 2:
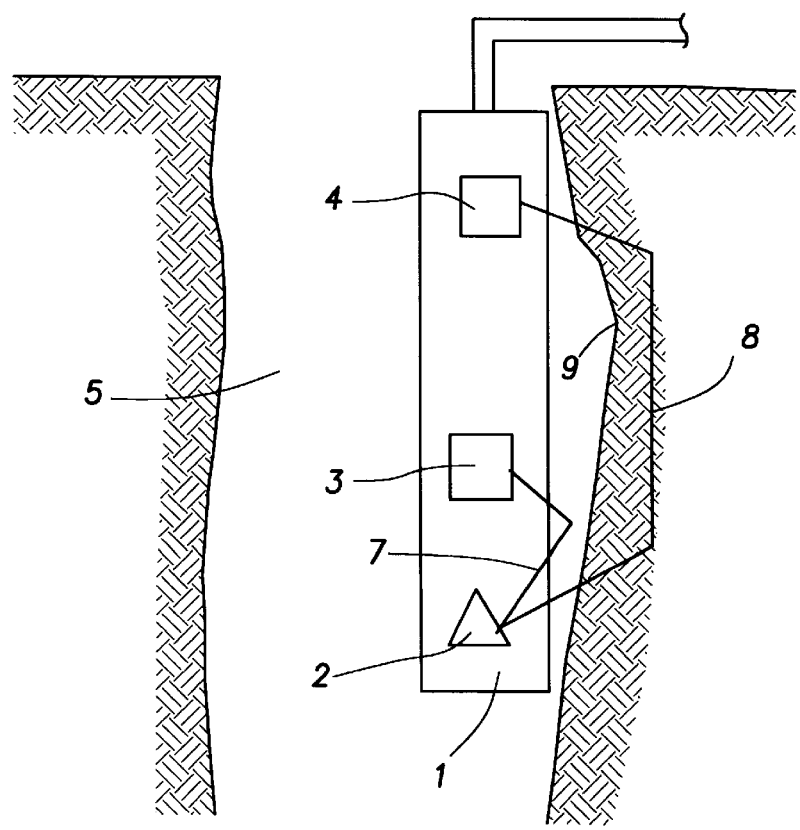
FIG. 2 is a diagram of a two-detector logging tool at large standoff caused by an irregular borehole shape.
Figure 3:
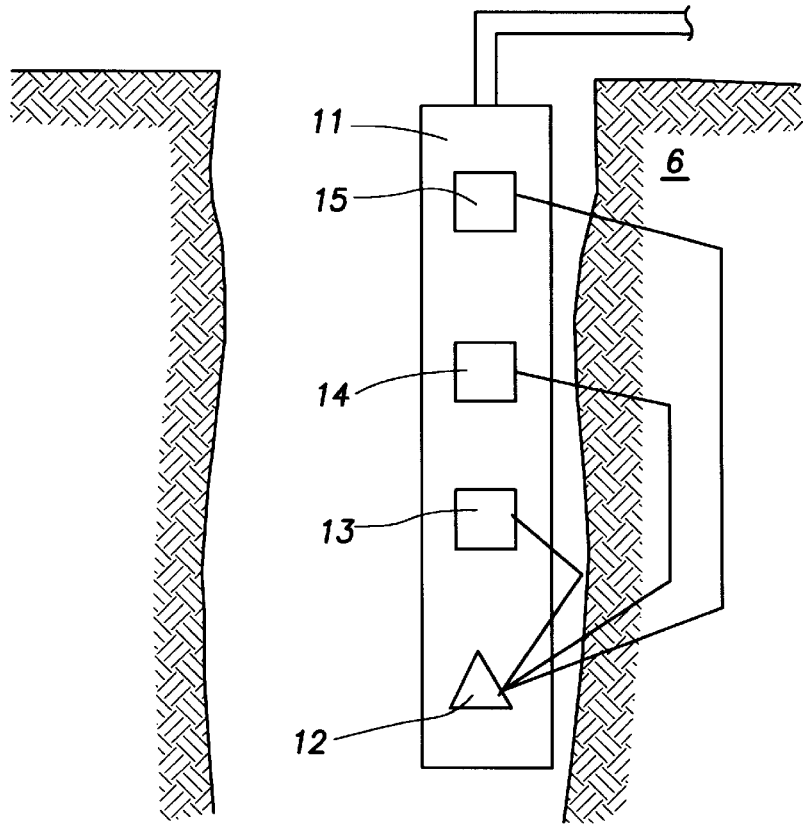
FIG. 3 is a view of the detection, by three detectors of gamma-rays scattered in the borehole and the formation.
Figure 5:
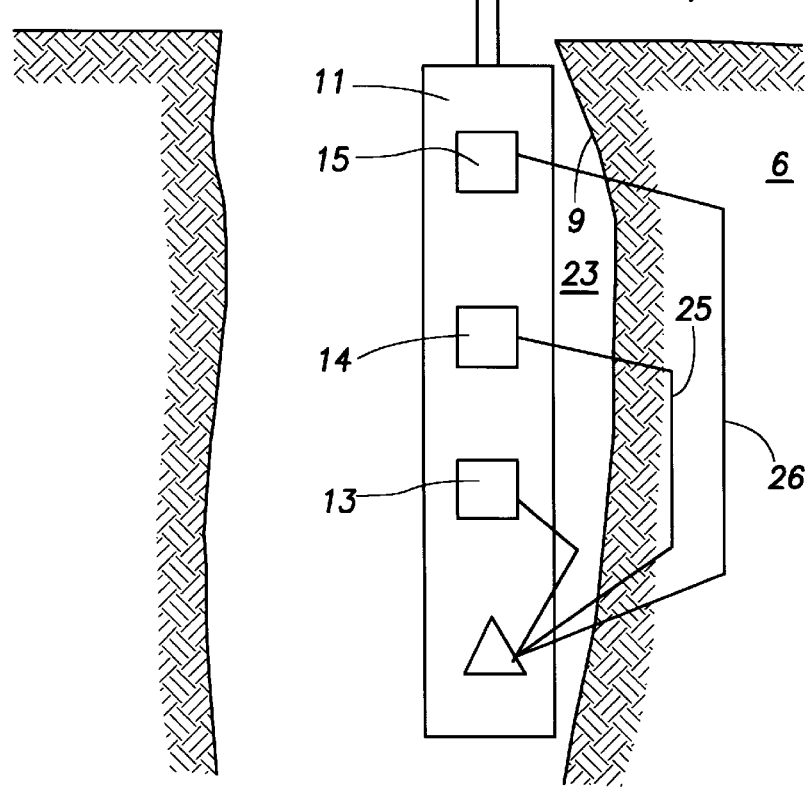
FIG. 5 is a diagram of the detection of signals using the present invention in an irregular borehole.

FIG. 5 shows the implementation of the present invention in a borehole causing large standoff from the borehole wall. Because of the shape of the borehole wall 9 a very large standoff 23 occurs between the tool 11 and the borehole wall 9. To overcome this large standoff, some detectors must have depths of investigation greater than the tool standoff. Detectors 14 and 15 have depths of investigation, 25 and 26 respectively, that extend into the formation 6 and provide for the measuring of the formation.

FIG. 6 shows the present invention in an irregular borehole with the detectors collimated. Collimation of the gamma-ray source and the detectors is optimized to ensure that all of the detectors have a different depth of investigation to enhance the standoff compensation. In addition, the collimation ensures that the tool is sensitive mainly to gamma-rays scattered in the formation or the region between the tool and the formation by only accepting gamma-rays incident from a certain direction. The gamma-ray source is also collimated, to cause gamma-rays to be emitted preferentially into the formation and to reduce the number of gamma-rays traveling in the borehole. As shown, the collimation angle 30 for the short-spaced detector 13 detects gamma-rays in the borehole and at shallow formation depths. The collimation angle 31 for the middle detector 14 picks up gamma-rays moving through the formation and also gamma-rays moving through the borehole. The collimation angle 32 for the long detector 15 picks up gamma-rays moving through formation at substantial depths as well as some gamma-rays from the borehole.

FIG. 7 shows a schematic cross section through the sonde section. The section contains the gamma-ray source 12 and three (3) gamma-ray detectors 13, 14 and 15 to detect the scattered gamma-rays. The gamma-ray source can either be a traditional chemical source ($^{137}$Cs, $^{60}$Co, or another suitable radio nuclide) or an electronic source (X-ray tube, betatron or other X-ray generating device). The gamma-ray detectors can be scintillation detectors (NaI, GSO or other scintillation materials) coupled to photomultipliers or other amplification devices. For some applications, semiconductor detectors or other detection devices may be preferable. In the present invention, the preferred gamma source is $^{137}$Cs and the detection of gamma-rays is preferably performed by NaI and GSO scintillation detectors. Collimation of the gamma-ray source and the detectors is optimized to ensure that all of the detectors have a different depth of investigation to enhance the standoff compensation.

In the present invention, the actual spacing of the detectors and in particular the spacing of the collimation openings from the source will influence the depth of investigation of the gamma-rays detected by each detector. The short spaced detector 13 has a spacing between 4 inches (10.16 centimeters) and 7 inches (17.78 centimeters) from a source 12. The middle detector 14 has a spacing of approximately 7 inches (17.78 centimeters) to 12 inches (30.48 centimeters) from the source. The long-spaced detector 15 has a spacing of approximately 12 inches (30.48 centimeters) to 18 inches (45.72 centimeters) from the source. The spacing refers to the vertical distance between the center of the source and the center of the detector. The collimation angle 30a for the short-spaced detector is recommended to be 30° to 60°. The middle-spaced detector front collimation angle 31a should be 35° to 90°. The long-spaced detector front collimation angle 32a, shown in FIG. 7, is between 45° to 90°. Referring to FIG. 8a, the short-spaced detector collimator opening 40 is usually a cylindrical or elliptical hole subtending and angle between ±5° to ±20°. As shown in FIG. 8b, the middle-spaced azimuthal opening 41 ranges from ±10° to ±35°. FIG. 8c shows an alternate opening 42 of the mid spaced detector. The long-spaced collimator opening 43 shown in FIG. 8d is between ±20° to ±50°. FIG. 8e shows an alternate opening 44 of the large spaced detector 15. The collimator azimuthal angles are short spaced<middle spaced<long spaced.

The objective of providing an improved means to detect the photo-electric effect of an earth formation is also affected by the detector collimation. This objective is accomplished as shown in FIG. 7. The gamma-ray source 12 is shielded and collimated with a collimator 33 to obtain a preferential gamma-ray emission toward the formation A window 34 of low density material is located in front of the source to maximize the number of primary gamma-rays emitted into the formation. The source is also collimated in such a way that the gamma-rays are emitted at an angle which improves the ability to scatter the gamma-rays towards the detectors through an opening in the side of the source collimator 35. The source is also shielded in a way that minimizes the number of gamma-rays emitted from the source into the borehole. This is accomplished by a cylindrical shield around the source and a thick shield 36 behind the source.

In FIG. 7, the short-spaced detector is designed to be sensitive to tool standoff by minimizing the azimuthal opening, such as 40 in FIG. 8, of the detector and by having the collimation 30a angled toward the source. The middle-spaced detector 14 is collimated to improve the sensitivity to the formation while remaining sensitive to the standoff region between the tool and the formation. Optimizing the middle-spaced detector collimation can also improve the detector's response to the photo-electric effect. Collimating the long-spaced detector 15 leads to a deeper depth of investigation. In addition, opening the long-spaced detector collimation azimuthally increases the count rates while keeping the borehole signal small.

The detectors can be NaI scintillators or preferentially GSO scintillators or other dense, fast scintillation materials. The preferred short-spaced detector is a GSO detector. The use of GSO allows the best shielding and collimation in a small tool and its high count rate capability makes it perfectly suited for the high counting rates encountered in the short-spaced detector. The use of the very compact integral detectors reduces the detector length and allows close spacing. The detector housings are made of high permeability magnetic material to provide shielding from magnetic fields. A window in the detector housing minimizes the attenuation of the gamma-rays entering through the collimation in front of the detector. The shielding and collimation material is usually a dense material of high atomic number (e.g. tungsten, lead or uranium). The gamma-rays traveling to the detector can cause this shielding material to emit X-rays which can be detected by the detector. These X-rays deteriorate the response to the photoelectric effect. They are suppressed by shielding the backside of the detector by a 0.5 to 2 mm thick layer of a material of intermediate Z (Z=30 to 60) which absorbs the undesired X-rays yet does not emit x-rays in the range of energies which are used for the measurement. Shielding may be inserted between the detectors to prevent gamma-rays entering through 1 collimator opening from traveling to the next detector after scattering in the first detector.

Algorithms for density and PEF can be of the spine-and -rib type as described in the Case and Ellis patents. Other algorithms can be forward modeling and inversion or use of the weighted multiple linear regression. The collimation of the middle-spaced and long-spaced detectors makes the tool suitable for a compensated photoelectric effect measurement (under evaluation) in the presence of muds which contain materials of high atomic number and which therefore exhibit a large photoelectric effect.

The apparatus and method of this invention provide significant advantages over the current art. The invention has been described in connection with its preferred embodiments. However, it is not limited thereto. Changes, variations and modifications to the basic design may be made without departing from the inventive concepts in this invention. In addition, these changes, variations and modifications would be obvious to those skilled in the art having the benefit of the foregoing teachings. All such changes, variations and modifications are intended to be within the scope of the invention which is limited only by the following claims.

We claim:

1. An apparatus for determining characteristics of an earth formation surrounding a borehole, comprising:
   a) a source for irradiating said earth formation with gamma radiation;
   b) short, mid, and long spaced detectors located in said apparatus, respectively, said detectors being capable of generating signals indicative of the energy of the gamma radiation detected by each of the detectors and said detectors being fixed successively at greater distances from said gamma radiation source such that each detector signal exhibits a negative response to increasing density of said formation;
   c) a housing that contains said gamma radiation source and detectors, said housing being capable of maintaining its mechanical properties in hostile borehole environments;
   d) a means for calculating formation density from said detector signals; and,
   e) a means for calculating the photo-electric factor of said earth formation from said detector signals.

2. The apparatus of claim 1 wherein one or more windows, of a material with a low atomic number, in said housing minimize attenuation of gamma-rays that enter said housing and are detected by said detectors.

3. The apparatus of claim 1 wherein each of said first, second and third detectors is uniquely collimated such that each detector detects gamma-rays from different depth ranges.

4. The apparatus of claim 1 wherein said short, mid and long spaced detectors have different depths of investigation into the formation, said depths of investigation increasing with detector distance from said gamma-ray source.

5. The apparatus of claim 1 further comprising shielding between said source and said detectors to prevent gamma-rays from traveling directly from the source to the detectors and shielding around portions of said detectors to shield said detectors from gamma radiation scattered in the borehole.

6. The apparatus of claim 1 wherein said housing is made of a high strength, low atomic number material.

7. The apparatus of claim 6 wherein said material is titanium.

8. The apparatus of claim 1 further comprising a detector housing for each of said detectors, said detector housing being of high permeability magnetic materials which shield each of said detectors from external magnetic fields.

9. The apparatus of claim 1 wherein said short spaced detector has a spacing from said source in the range of 4 inches to 7 inches, the middle detector has a spacing from approximately 7 inches to 12 inches and said long detector has a spacing from approximately 12 inches to 18 inches.

10. The apparatus of claim 3 wherein said gamma radiation source is collimated such that gamma radiation emitted by said source into said formation is directed preferentially into the formation at such an angle as to enhance the scattering towards the detectors in the tool.

11. The apparatus of claim 10 further comprising shielding between the detectors to prevent gamma-rays scattered in one detector from entering the next detector.

12. The apparatus of claim 10 wherein said collimation for the short spaced detector is comprised of a small cylindrical opening at an angle of approximately 30 degrees to 60 degrees with respect to the tool axis, wherein the collimation of the mid spaced detector is comprised of an azimuthal opening of ±10 degrees to ±30 degrees and a forward opening angled at approximately 30 degrees to 60 degrees and the long spaced detector collimation having an azimuthal angle of ±20 to ±50 degrees.

13. The apparatus of claim 12 wherein the azimuthal openings of the detectors increase with increasing distance from the source.

14. The apparatus of claim 1 where said first detector uses a GSO scintillation detector and the other detectors are NaI.

15. The apparatus of claim 1 wherein all detectors are GSO detectors.

16. The apparatus of claim 1 wherein all detectors are NaI.

17. An apparatus for determining characteristics of an earth formation surrounding a borehole, comprising:
 a) a source for irradiating said earth formation with X-ray radiation;
 b) short, mid, and long spaced detectors located in said apparatus, respectively, said detectors being capable of generating signals indicative of the energy of the radiation detected by each of the detectors and said detectors being fixed successively at greater distances from said X-ray radiation source such that each detector signal exhibits a negative response to increasing density of said formation;
 c) a housing that contains said X-ray radiation source and detectors, said housing being capable of maintaining its mechanical properties in hostile borehole environments;
 d) a means for calculating formation density from said detector signals; and
 e) a means for calculating the photo-electric factor of said earth formation from said detector signals.

18. A method of determining characteristics of an earth formation surrounding a borehole, comprising the steps of:
 a) collimating a radiation source and short, mid, and long spaced detectors such that radiation emitted by said source into said formation is directed preferentially into the formation and at such an angle as to enhance scattering towards radiation detectors positioned in said borehole at progressively farther distances from said radiation source and each detector signal exhibits a negative response to increasing density of said formation;
 b) irradiating said formation with gamma rays from said radiation source;
 c) generating gamma-ray spectra from gamma rays detected at each of said detectors;
 d) computing an apparent density from the spectra in each detector; and
 e) measuring a photo-electric effect from the spectrum of each detector.

19. The method of claim 18 further comprising the step of computing a true formation density from said apparent density.

20. The method of claim 18 further comprising the step of computing the standoff distance between an apparatus containing said detectors and source and a wall of said borehole from the spectra of all three detectors.

21. The method of claim 20 further comprising the step of compensating said photoelectric effect to account for said apparatus standoff.

22. The method of claim 20 wherein said formation density, standoff and formation photo-electric effect are computed from a forward model of the density, standoff and photo-electric effect and subsequent inversion of the forward model.

23. The method of claim 18 further comprising before step (e), the step of optimizing the mid detector collimation to improve the response of the mid detector to the photo-electric effect of the formation.

* * * * *